United States Patent [19]

Stoughton

[11] Patent Number: 5,177,565
[45] Date of Patent: Jan. 5, 1993

[54] REFLECTANCE MEASUREMENT APPARATUS WITH NOISE REDUCTION CIRCUITRY

[75] Inventor: John W. Stoughton, Indianapolis, Ind.

[73] Assignee: United Medical Manufacturing Company, Indianapolis, Ind.

[21] Appl. No.: 653,765

[22] Filed: Feb. 11, 1991

[51] Int. Cl.⁵ ............................................. G01N 21/47
[52] U.S. Cl. ..................................... 356/446; 356/447
[58] Field of Search ............................... 356/445-448, 356/41, 402-411; 128/689-690; 422/82.05

[56] References Cited

U.S. PATENT DOCUMENTS 4,258,719  3/1981  Lewyn ................................ 128/690
4,800,885  1/1989  Johnson ............................... 356/41

OTHER PUBLICATIONS

Excerpt from Book by M. S. Roden Entitled *Analog and Digital Communications Systems*, Englewood Cliffs: Prentice-Hall, 1979.
Excerpt from Book by C. D. McGillem and G. R. Cooper Entitled *Continuous and Discrete Signal and System Analysis*, New York: Holt, Rinehart and Winston, Inc., 1974.

Primary Examiner—F. L. Evans
Assistant Examiner—K. P. Hantis
Attorney, Agent, or Firm—Woodward, Emhardt, Naughton Moriarty & McNett

[57] ABSTRACT

A reflectance meter having improved noise immunity for measuring photometric quantities is disclosed. The device includes noise reduction techniques for eliminating the effects of ambient and artificial light upon the measurement signal. A gated modulator provides frequency shifting of desired information to a carrier frequency so that undesired signals may be filtered out. A gated demodulator provides a means to demodulate the information contained in frequency spectrum near the gate or chopping frequency.

2 Claims, 3 Drawing Sheets

REFLECTANCE MEASUREMENT APPARATUS WITH NOISE REDUCTION CIRCUITRY

FIELD OF THE INVENTION

This invention relates to reflectance meters, and more specifically to reflectance meters incorporating electronic noise reduction techniques.

BACKGROUND OF THE INVENTION

The use of the meters for monitoring blood glucose levels is a well established means of improving insulin control for diabetic persons. Other applications of reflectance meters for measuring remission characteristics or diffuse reflection characteristics of a chemically treated reagent strip are also well known. A typical reflectance meter includes a light source for illuminating a target, a photo-detector for detecting light reflected from the target, and reagent strip targets which provide an indication of chemical makeup of a solution. The target strips provide a color change which corresponds with a particular chemical concentration in such a fashion that a very repeatable color change occurs when a particular concentration of a target chemical in solution is detected. Normally, the light source and the light detector are keyed to a particular wavelength of light or range of wavelengths so as to accurately measure the color change in the reagent treated strip. The wavelength of light corresponding to the color to be detected and produced by the strip may be in the visible light range or outside the visible light range in the infrared region. It is also well known that electro-magnetic radiation or light having identical wavelengths are also found in ambient light or sunlight as well as in artificial light produced by electrical light fixtures. The reliability and repeatability of a reflectance meter is seriously impacted by extraneous light which creates electronic noise in the measured signal. A reflectance meter which incorporates circuitry to reduce or eliminate the effects of ambient and artificial lighting is needed.

SUMMARY OF THE INVENTION

A reflectance measuring device according to one aspect of the present invention comprises light source means for illuminating a target, photo-detector means for producing a signal corresponding to light appearing on the target, power source means connected to the light source and supplying a power signal to the light source, an oscillator for producing an oscillator signal, a high pass filter connected to the output of the photo-detector, the high pass filter having a cutoff frequency below the oscillation frequency of the oscillator, the high pass filter producing a filtered output signal, circuit means for modulating the power signal to produce a periodic power signal centered about the frequency of the oscillator signal, demodulator means for producing a gated demodulator output signal from periodic signals present in the filtered output signal, and a low pass filter for filtering the gated demodulator output signal to produce a noise free signal, the low pass filter having a cutoff frequency below 60 hertz.

One object of the present invention is to provide an improved reflectance meter.

Another object of the present invention is to provide noise reduction circuitry to reduce the effects of ambient light and artificial light upon the reflectance meter.

A further object of the present invention is to provide a low cost, economical noise reduction circuit for use in a reflectance meter to provide results which are repeatable under adverse lighting conditions.

These and other objects will become more apparent from the following description of the preferred embodiment.

DESCRIPTION OF THE PREFERRED EMBODIMENT

Figure 1:
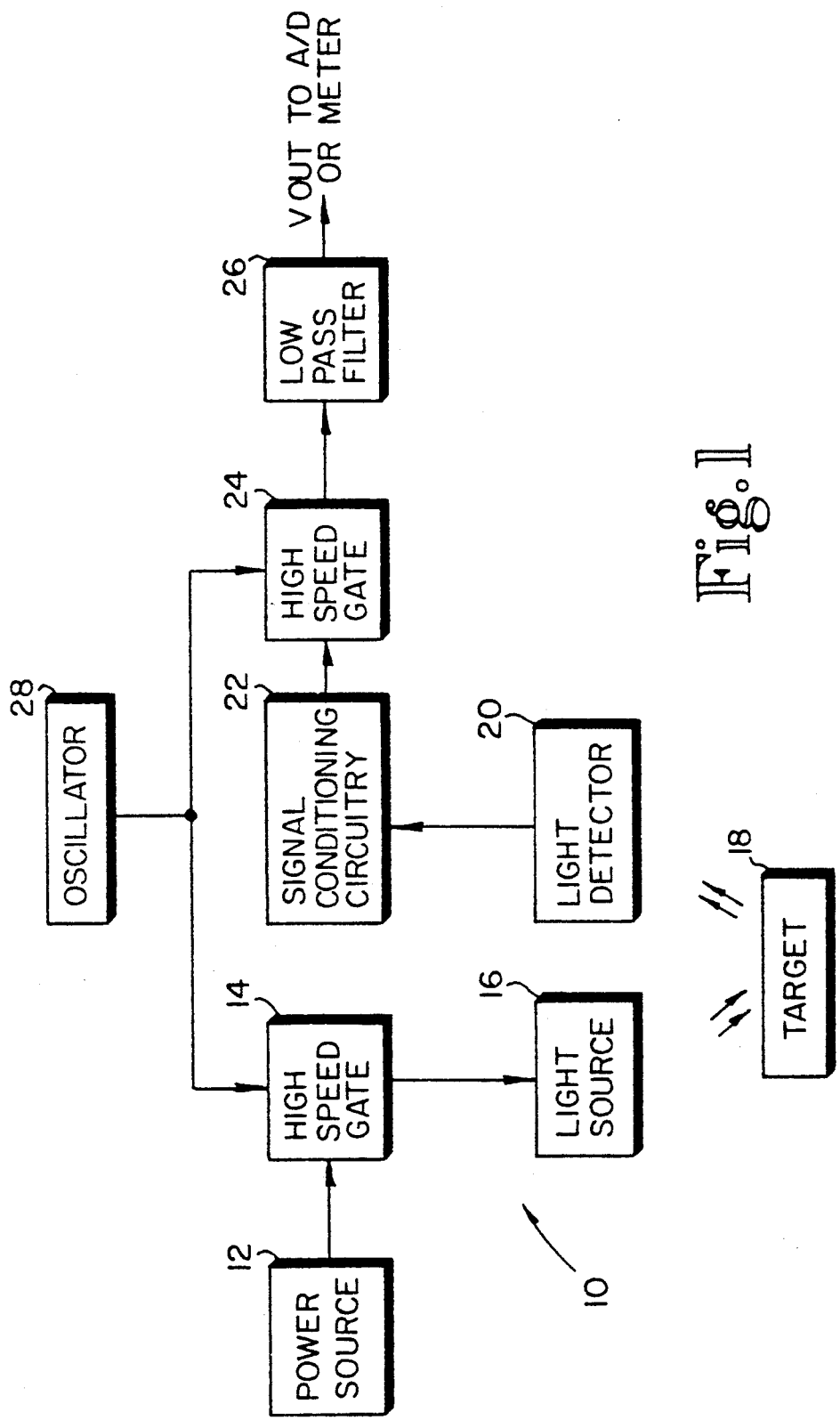
FIG. 1 is a block diagram of the improved reflectance meter according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, a reflectance measuring apparatus or device 10 according to the present invention is shown. The device 10 includes a power source 12 which supplies a power signal to an input of high speed gate 14. High speed gate 14 acts as an electronic switch, and when activated provides a virtual short circuit from power source 12 to light source 16. Light source 16 produces a light signal which is directed toward target 18. The light signal produced by light source 16 varies in intensity in accordance with power signals received from gate 14. Light detector 20 is sensitive to light reflected from target 18 and produces an electrical signal corresponding to the illumination or photon intensity of target 18, which is supplied to signal conditioning circuitry 22. The signal conditioning circuitry 22 includes an amplifier and a high pass filter. The amplifier provides gain for the signal from light detector 20. The high pass filter reduces the magnitude of lower frequencies and supplies the filtered signal to an input of high speed gate 24. High speed gate 24 functions identically as high speed gate 14 in that it acts as an electronic switch. When activated, high speed gate 24 supplies the signal received from signal conditioning circuitry 22 to an input of low pass filter 26. Oscillator 28 provides a switching signal to high speed gates 14 and 24 and essentially operates the high speed gates to chop the power source signal and the output of the signal conditioning circuitry at a high speed rate. Low pass filter 26 provides a low pass filtering function for signals from the high speed gate 24. The output of low pass filter 26 is supplied to an analog to digital converter forming a part of a microprocessor based analysis system (not shown) or to a visual indicator such as a meter (not shown).

Target 18 is typically a reagent strip chemically treated to respond with a coloration change in accordance with the chemical for which analysis is sought. The coloration change may be one visible to the naked eye, i.e. in the visible light range, or outside the visible light range. Oscillator 28, in the preferred embodiment, supplies a ten kilohertz signal to the control or enable inputs of high speed gates 14 and 24. Gates 14 and 24 are synchronously switched on and off by the signal from oscillator 28.

Operationally speaking, power source 12 supplies a predetermined power signal to light source 16 through high speed gate 14 to produce a modulated illumination intensity level of a known reference value. Simultaneously, oscillator 28 causes high speed gate 14 to switch on and off to chop the signal from power source 12 into a squarewave signal. The duty cycle of the oscillator signal can range anywhere from one to 99 percent theoretically, however a duty cycle of 50 percent will provide good results.

A light source 16 is selected to emit a particular wavelength of light. This is necessary in order to properly analyze the color change of the target 18. Light detector 20 receives the modulated photon reflections from target 18 and produces an electrical signal corresponding thereto which is supplied to an input of signal conditioning circuitry 22. Circuitry 22 amplifies the signal from the light detector 20 and provides a high pass filtering function to filter the frequency spectrum below two kilohertz. Since the typical noise information produced by ambient light and artificial lighting sources will be centered about zero hertz, 60 hertz, and 120 hertz, a high pass filter circuit with a cutoff frequency of approximately two kilohertz will effectively reduce or eliminate the noise information present below 200 hertz.

The amplified and filtered signal produced by circuitry 22 is supplied to high speed gate 24 wherein the signal is chopped at the rate of oscillator 28's output. After chopping, the signal is supplied to low pass filter 26 which typically has a cutoff frequency of approximately 10 hertz. The high speed gate 24 is a gated demodulator for demodulating information from the 10 kilohertz spectral region down to the zero hertz region. Thus, the information which is modulated onto the 10 kilohertz signal by the transmitter portion of the device 10, i.e. the power source 12, high speed gate 14 and light source 16, is demodulated from 10 kilohertz back to a usable signal for analysis by way of the gated demodulator comprised of high speed gate 24 and low pass filter 26. Analysis of the signal appearing at the output of low pass filter 26 is accomplished via analog to digital converter and microprocessor hardware to provide accurate and reliable analysis of the quantity of photons reflected from target 18.

An analysis of the Fourier transform of a periodic function corresponding to the output of light detector 20 is discussed in great detail in a book by M. S. Roden entitled Analog and Digital Communications Systems, Englewood Cliffs: Prentice-Hall, 1979. A discussion of gated demodulation techniques may be found in Continuous and Discrete Signal and System Analysis by C. D. McGillem and G. R. Cooper, New York: Holt, Rinehart and Winston, Inc., 1974. Both of these publications are hereby incorporated by reference in the present application.

Figure 2:
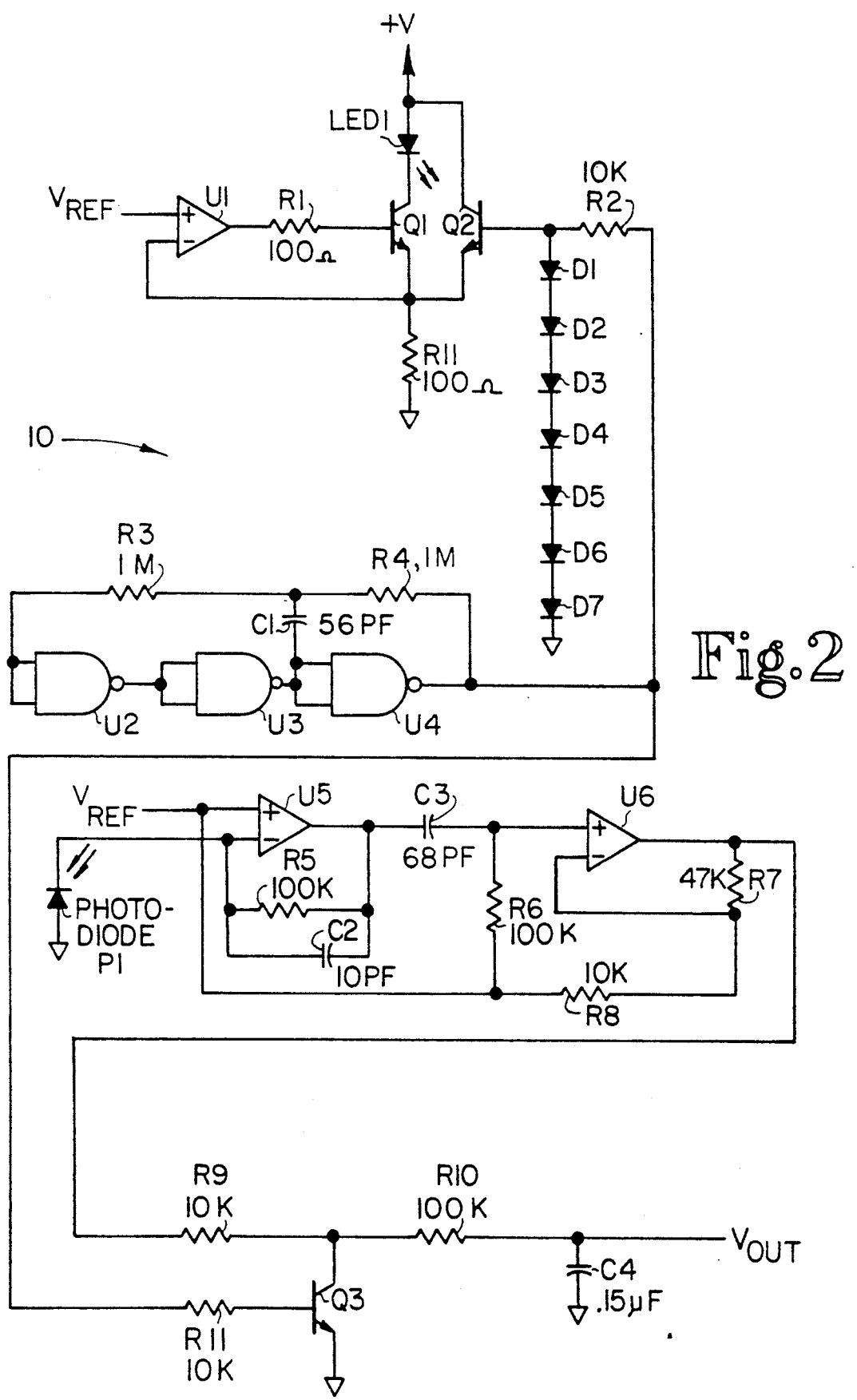
FIG. 2 is a schematic diagram of the reflectance meter according to the present invention.

Referring now to FIG. 2, a schematic diagram of one embodiment of the reflectance measuring device 10 according to the present invention is shown. Correspondence between FIGS. 1 and 2 is as follows. Power source 12 is represented by operational amplifier (op amp) U1, transistor Q1 and associated passive circuit components to provide a bias current for LED1. LED1 corresponds to light source 16. High speed gate 14 corresponds to transistor Q2. Oscillator 28 is represented by logic gates U2, U3 and U4 which are NAND gates. Diodes D1-D7 limit the bias voltage to the base of transistor Q2 to approximately 5 volts. Light detector 20 is represented by a photo-detector device also known as a photodiode which is designated P1. Signal conditioning circuitry 22 includes the op amp circuit U5, the high pass filter comprised of capacitor C3 and R6, and op amp circuit U6 which provides additional signal voltage gain. High speed gate 24 is represented by transistor Q3. Low pass filter 26 is comprised of resistor R10 and capacitor C4.

Op amps U1, U5 and U6 are single-sided power supply op amps such as an LM324 available from National Semiconductor. Logic gates U2, U3 and U4 are 74HC00 low power logic gates which are TTL compatible and available from a variety of sources well known in the art. LED1 is a model number LDH5023 and photodiode P1 is a model number SFH206K, both available from Siemens.

The voltage $V_{REF}$ supplied to the positive input of op amp U1 and op amp U5 is a fixed reference voltage which may be created using techniques well known in the art. Voltage $V_{REF}$ provides a reference voltage signal often referred to as a pseudo-ground or virtual ground. Such a reference signal is necessary when using a single sided power supply with single sided op amps such as the LM324 series. In a preferred embodiment of the invention, $V_{REF}$ is 2.5 volts and the power supply voltage V+ (present at the anode of LED1) is 12 volts DC. The bias current established through LED1 is approximately 25 milliamps. Transistors Q1 and Q2 may be any of a variety of NPN transistors, one example is a 2N2222 transistor. Diodes D1-D7 are 1N4148 diodes or other suitable substitute.

The 10 kilohertz oscillator signal present at the output of logic gate U4 causes transistor Q2 to switch on and off at a rate corresponding to the frequency of oscillation of the oscillator circuit. In addition, transistor Q3 is switched on and off at the same rate. Thus, the optical intensity of the light emanating from LED1 is modulated based upon the oscillation frequency of the oscillator. The modulated light is reflected off a target (not shown in FIG. 2) and detected by photodiode P1. Op amp U5 provides voltage gain for the signal from photodiode P1. Capacitor C3 and resistor R6 form a high pass filter with a cutoff frequency of approximately two kilohertz. The noise information below 200 hertz at the non-inverting input of op amp U6 is substantially attenuated. The filtered signal is amplified by op amp U6 and supplied to the low pass filter circuit consisting of resistor R10 and C4. Transistor Q3 is continuously switching on and off to gate demodulate the signal present at the output of op amp U6. The gated demodulation technique transfers the frequency information centered about 10 kilohertz back down to a center frequency of approximately zero hertz. The cutoff frequency for the low pass filter comprised of resistor R10 and capacitor C4 is approximately 10 hertz. The signal labelled $V_{OUT}$ is supplied to an input of an analog to digital converter or other signal analysis circuitry for determining the quantity of photons reflected from the target 18.

Figure 3:
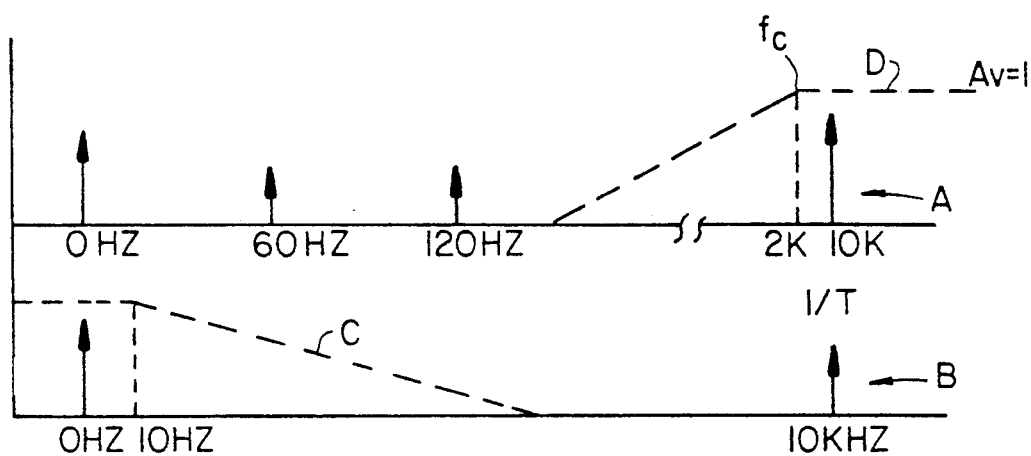
FIG. 3 is a graph showing the spectral relationship of the signal, the noise and the frequency shifted signals of the present invention.

Referring now to FIG. 3, two spectral charts depicting signal spectrums are shown. As shown in chart A, during continuous illumination of target 18 by light source 16, the information at zero hertz includes desired photometric signals and ambient light noise, whereas the 60 hertz and 120 hertz components are artificial noise attributable to artificial light sources. The signals present at 10 kilohertz are the photometric quantities detected by light detector 20 when the oscillator 28 gates the power source 12 on and off. By frequency shifting the information corresponding to the photometric reflectance of target 18 up to the 10 kilohertz region, it is readily understood how the high pass filter, having a cutoff frequency of approximately two kilohertz, will eliminate the ambient and artificial noise in the frequencies below 200 hertz. Referring now to the lower chart B. the spectral lines shown at 10 kilohertz and zero hertz represent the frequency shifting which is accomplished by the gated demodulation technique. The gated demodulator shifts the frequency information about the 10 kilohertz spectral region down to the zero hertz spectral region. Thus, the information relating to the photometric reflectance of target 18 becomes available for easy analysis by implementing a low pass filter 26 having a cutoff frequency substantially below 10 kilohertz, i.e. a filter having a cutoff frequency of approximately 10 hertz. The transfer function of such a filter is represented by broken line C. Similarly, the broken line D represents the transfer function of the high pass filter which is part of circuitry 22 and represented by capacitor C3 and resistor R6 in FIG. 2.

Recognized advantages of the noise immunity circuit of the present invention include increased protection against radio frequency interference as well as reduced current consumption in that the required current for modulation and demodulation is less than the LED current saved by chopping the drive current. In addition, LED die heating is reduced and current handling capability increased due to the pulsed current supplied to the LED. Maintaining the LED die at a lower temperature prevents color changes due to temperature drift which typically occur when the die is heated. Maintaining the die at a lower temperature results in lower errors in remission reading due to LED heating and the resultant color drift attributable to the temperature change.

Quite often the chemical in solution whose concentration is measured by the device according to the present invention is glucose or sugar. Another common use of reflectance meters is for detecting pollutants in water. Any reflectance measuring device for quantizing or measuring detectable colorization changes in a reagent strip is contemplated as a possible application of the present invention. Reagent strips made of transparent or translucent polymers are particularly troublesome when ambient light may interfere with the reflectance meter measuring process. Thus, reduction of ambient light interference greatly increases the accuracy of measurement by the device according to the present invention when reagent strips which "light pipe" or transmit light through the strip must be used.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:
1. A reflectance measuring device comprising:
   a photo-detector situated to detect light reflecting from a chemically treated target strip and producing an electrical signal in accordance with the intensity of light striking said photo-detector;
   a light source having a power input, said light source directed toward the target strip;
   an oscillator which produces an oscillator signal;
   a power source connected to said power input of said light source, said power source supplying a periodic power signal in accordance with said oscillator signal to said power input;
   amplifier means responsive to said electrical signal and producing an amplified electrical signal;
   a band pass filter responsive to said amplified electrical signal having an upper cutoff frequency below the frequency of oscillation of said oscillator and a lower cutoff frequency above zero hertz; and
   wherein said light source produces light in a predetermined range corresponding to a particular colorization response of a chemically treated target strip.

2. The device of claim 1 wherein said power source supplies a fixed current signal to said light source when activated, and said light source is a light emitting diode.

* * * * *